United States Patent [19]
Hanson

[11] Patent Number: 5,885,074
[45] Date of Patent: Mar. 23, 1999

[54] LIGATURES FOR ORTHODONTIC APPLIANCES AND ORTHODONTIC BRACKETS INCORPORATING SUCH LIGATURES

[76] Inventor: Eric H. Hanson, 33 Woodside Drive, Hamilton, Ontario, Canada, L8T 1C4

[21] Appl. No.: 958,796

[22] Filed: Oct. 27, 1997

[51] Int. Cl.[6] .................................................. A61C 3/00
[52] U.S. Cl. ................................................ 433/13; 433/15
[58] Field of Search .................................. 433/8, 10, 11, 433/13, 14, 15, 21; 267/74, 167

[56] References Cited

U.S. PATENT DOCUMENTS

| | | |
|---|---|---|
| 2,991,064 | 7/1961 | De Jean . |
| 3,593,421 | 7/1971 | Brader .......................................... 433/8 |
| 3,633,277 | 1/1972 | Reichel ....................................... 433/13 |
| 3,691,635 | 9/1972 | Wallshein ................................... 433/21 |
| 3,878,609 | 4/1975 | Wallshein ..................................... 433/2 |
| 3,961,421 | 6/1976 | Wallshein ................................... 433/11 |
| 3,964,165 | 6/1976 | Stahl .......................................... 433/14 |
| 4,086,702 | 5/1978 | Wallshein ................................... 433/21 |
| 4,260,375 | 4/1981 | Wallshein ................................... 433/11 |
| 4,522,590 | 6/1985 | Pletcher ..................................... 433/15 |
| 4,849,032 | 7/1989 | Kawaguchi ................................. 433/21 |
| 5,269,681 | 12/1993 | Degnan ...................................... 433/15 |

*Primary Examiner*—Ralph A. Lewis

[57] ABSTRACT

A ligature for an orthodontic appliance comprising a coil spring hoop of helically wound metal strip or wire or a wave spring hoop of wave wound metal strip or wire, preferably of shape memory metal. Such a metal ligature is simpler and more convenient to use than wire ties and has a life considerably longer than the elastomeric ligatures currently in use; because of this extended life they can be permanently attached to a bracket body to provide a self-ligating bracket. A coil wound ligature has the form of a hoop and is attached to the bracket body via a U-shaped core member threaded through part of the hoop and having its ends fastened to the bracket body. The ligature may have the form of a loop having its ends inserted in respective bores in the bracket body. The ligature may comprise an attachment part by which it is attached to the bracket body and a loop retainer part engageable over a bracket tie wing, the attachment and retainer parts being connected together by two mesially-distally spaced wave wound spring parts.

19 Claims, 4 Drawing Sheets

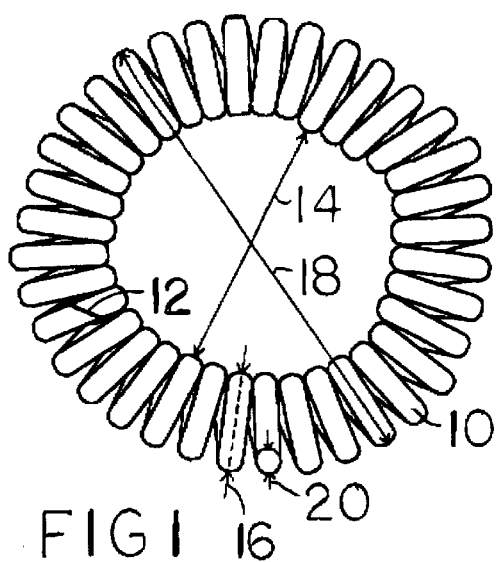
FIG 1
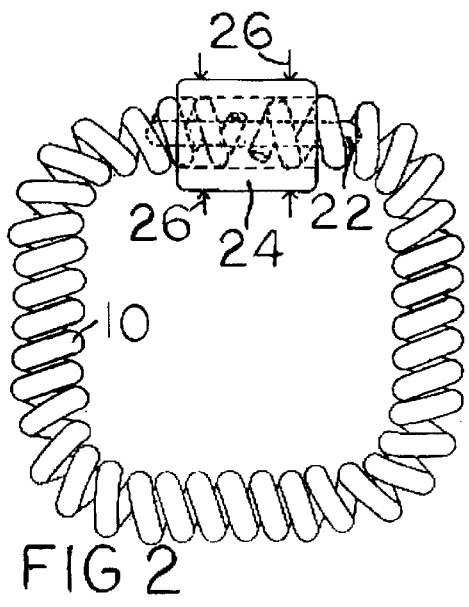
FIG 2
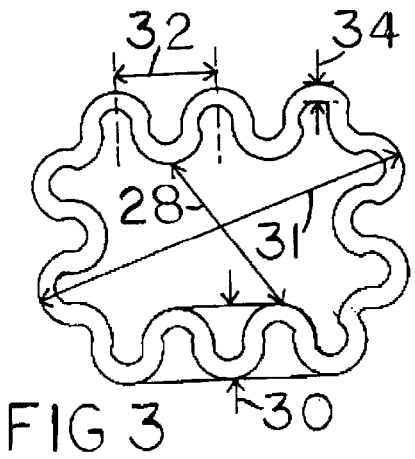
FIG 3
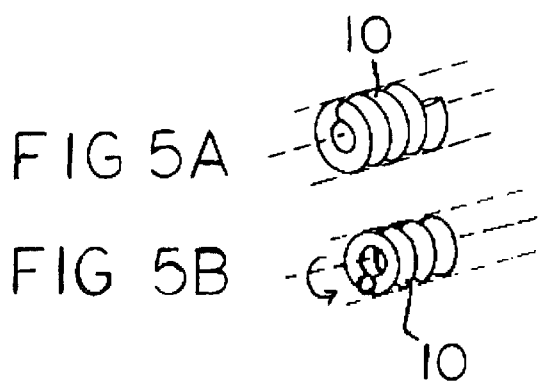
FIG 5A
FIG 5B
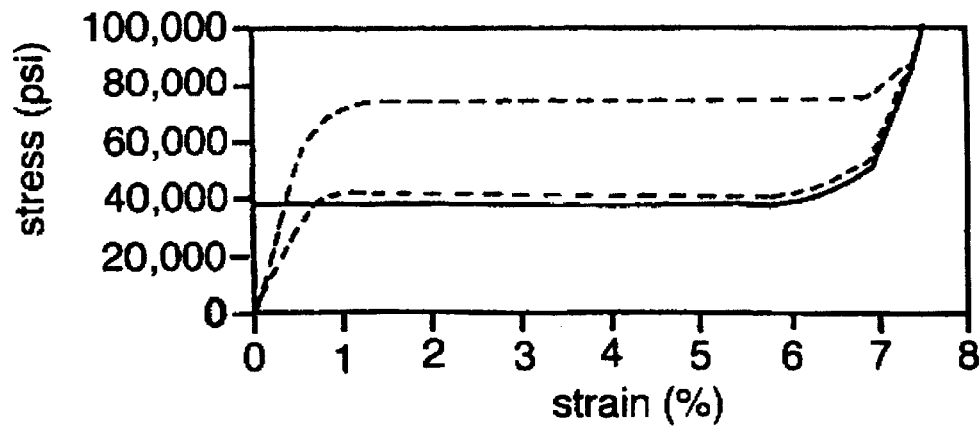
FIG 4

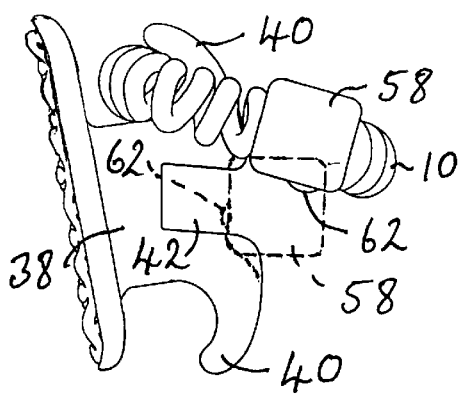
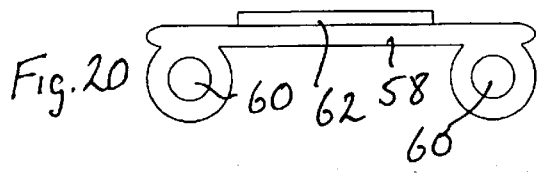
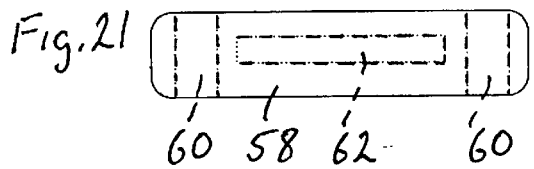
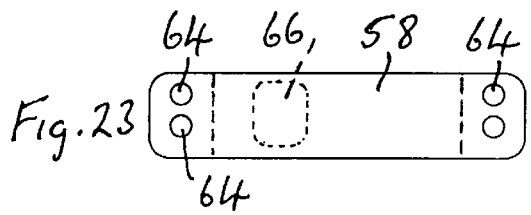
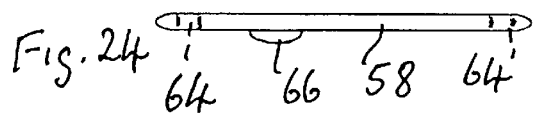
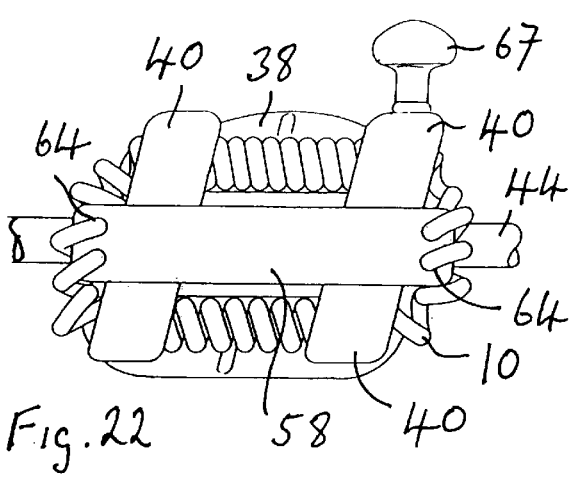
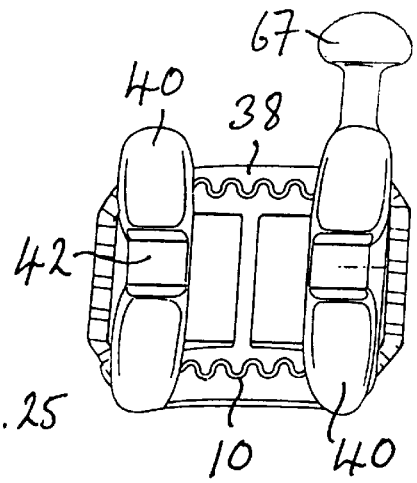
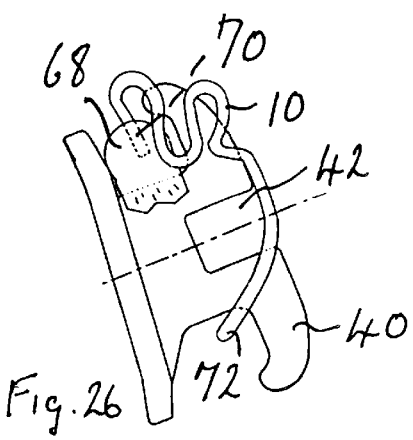
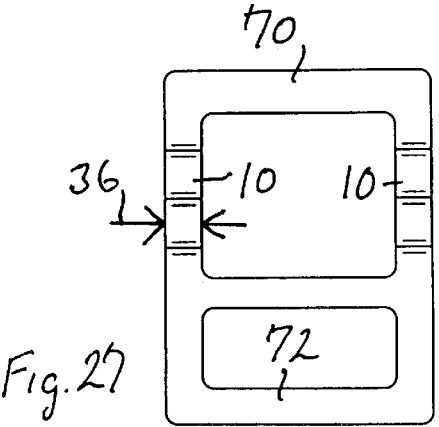

LIGATURES FOR ORTHODONTIC APPLIANCES AND ORTHODONTIC BRACKETS INCORPORATING SUCH LIGATURES

FIELD OF THE INVENTION

This invention is concerned with new ligatures for orthodontic appliances, and new self-ligating orthodontic brackets which comprise ligating means as an integral part thereof.

REVIEW OF THE PRIOR ART

The majority of orthodontic procedures employ a plurality of brackets that are attached to selected teeth, usually by cementing them thereto, together with an arch wire, so called because it is preformed to an optimum arch shape corresponding to the desired conformation of the teeth at the conclusion of the procedure, the wire being engaged in mesial distal extending slots in the brackets. The arch wire is attached to the brackets by respective ligating means and, when these procedures were first introduced, each ligating means usually consisted of a soft metal wire that was twisted about the bracket and the arch wire. Subsequently polyurethane elastomeric materials were developed suitable for the environment of the human mouth and hoops or O-rings made of these materials are increasingly commonly used.

In another line of development each bracket comprises its own ligating metal spring member permanently mounted on the bracket body for movement between slot open and slot closed positions; specific examples of such self ligating brackets are those disclosed and claimed in U.S. Pat. Nos. 3,772,787; 4,248,588; 4,492,573; and 5,630,716 of G. Herbert Hanson, the disclosures of which are incorporated herein by this reference.

The ease and convenience of use of the polyurethane hoop ligatures have led to their wide adoption, but they have a relatively short life, to the extent that patients must make regular appointments at quite short intervals, e.g. from one to four weeks, at which they can be inspected to ensure that they are still effective; it is found in practice that usually they must be changed at each appointment. Any such visit is inconvenient and time consuming both for the orthodontists and the patients, and also somewhat stressful, especially for child patients. In an attempt to reduce such stress the hoop ligatures are sometimes made available in a variety of colors, so that the child can at each visit request a color to suit the season, e.g. black at Halloween and red at Christmas. It would be preferable to be able to provide instead a hoop ligature with a considerably longer life, ideally one that would survive for the life of the procedure. The number of visits could then be reduced to that required to ensure that the procedure is progressing satisfactorily.

SUMMARY OF THE INVENTION

It is a principal object of the invention therefore to provide new orthodontic ligating hoops of metal, so that they have the possibility of longer effective lives than equivalent hoops of elastomeric materials.

It is another principal object to provide new brackets having as an integral part thereof ligating means consisting of a hoop or loop of metal.

In accordance with the invention there is provided a ligature for an orthodontic appliance comprising a hoop shaped coil spring of metal strip or wire having a corresponding hoop shaped axis, the metal strip or wire being wound helically about the hoop shaped axis;

wherein the unstrained hoop shaped coil has an inside diameter in the range from 1 mm to 5 mm (0.04 in to 0.20 in) and the helically wound coil has an outside diameter in the range 0.40 mm to 1.0 mm (0.016 in to 0.040 in).

Also in accordance with the invention there is provided an orthodontic bracket comprising:

a bracket body having labial, lingual, gingival, occlusal, mesial and distal surface portions, the body having a mesial distal extending arch wire slot opening to the labial surface portion; and a ligature attached to the body and movable on the body between open and closed positions in which the slot opening is respectively open for insertion of an arch wire into the slot and its removal therefrom and is closed by the ligature to retain an archwire therein;

the ligature comprising a hoop or loop shaped coil spring of metal strip or wire and having a corresponding hoop or loop shaped axis, the metal strip or wire being wound helically about the hoop or loop shaped axis.

Preferably the metal strip or wire has a diameter, or an effective diameter as defined, or in the range from 0.125 mm to 0.23 mm (0.005 in to 0.009 in).

Further in accordance with the invention there is provided a ligature for an orthodontic appliance comprising a hoop shaped wave spring of metal strip or wire, the metal strip or wire being formed to a repeated successive wave shape along the length of the hoop;

wherein the unstressed hoop has an inside diameter in the range from 1 mm to 5 mm (0.04 in to 0.20 in) and the amplitude of the waves of the wave wound strip or wire of the hoop is in the range 0.375 mm to 1.0 mm (0.015 in to 0.040 in).

Further in accordance with the invention there is provided an orthodontic bracket comprising:

a bracket body having labial, lingual, gingival, occlusal, mesial and distal surface portions, the body having a mesial distal extending arch wire slot opening to the labial surface portion; and a ligature attached to the body and movable on the body between open and closed positions in which the slot opening is respectively open for insertion of an arch wire into the slot and its removal therefrom and is closed by the ligature to retain an archwire therein;

the ligature comprising a hoop or loop shaped wave spring of metal strip or wire, the metal strip or wire being formed to a repeated successive wave shape along the length of the hoop or loop.

Preferably the metal strip or wire has a thickness in the range from 0.075 mm to 0.30 mm (0.003 in to 0.012 in) and a width in the range from 0.25 mm to 0.75 mm (0.010 in to 0.030 in).

DESCRIPTION OF THE DRAWINGS

Particular preferred embodiments of the invention will now be described, by way of example, with reference to the accompanying diagrammatic drawings, wherein:

FIG. 1 is a front elevation of a first embodiment comprising a coil spring hoop ligature of helically wound metal strip or wire;

FIG. 2 is a front elevation of a second embodiment also comprising a coil spring hoop ligature of helically wound metal strip or wire;

FIG. 3 is a front elevation of a further embodiment comprising a wave wound spring hoop ligature of wave wound metal strip or wire;

FIG. 4 is a stress-strain graph of a typical shape memory metal alloy illustrating the effect of stress preload on its characteristic;

FIG. 5A is a perspective side view of a part of a helically wound coil prior to winding to preload it;

FIG. 5B is a perspective side view similar to FIG. 3A showing the helically wound coil part subsequent to winding to preload it;

FIG. 19 is a mesial or distal elevation similar to FIG. 18 comprising a different attachment providing for specific control of sliding friction;

FIGS. 20 and 21 are views respectively from the occlusal or gingival and the labial of the attachment employed in the embodiment of FIG. 19;

FIG. 22 is an elevation from the labial showing another way of combining a coil spring ligature hoop of the invention with an attachment thereto to provide friction-free operation of the orthodontic procedure, the ligature being in slot closed position;

FIGS. 23 and 24 are views respectively from the occlusal or gingival and the labial of an attachment employed in the embodiment of FIG. 22 and providing for specific control of sliding friction;

FIG. 25 is an elevation from the labial of a bracket showing the application thereto of a wave spring ligature of FIG. 3;

FIG. 26 is a mesial or distal elevation of a bracket showing a wave spring ligature of special form permanently attached thereto and in slot closed position; and FIG. 27 is an elevation from the labial of the wave spring ligature of FIG. 26.

DESCRIPTION OF THE PREFERRED EMBODIMENTS

Figure 6:
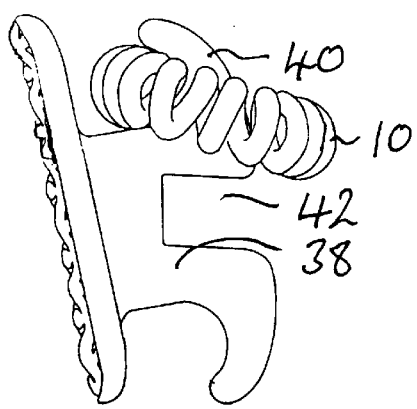
FIG. 6 is a mesial or distal elevation of a bracket illustrating one way of mounting a coil spring ligature on the bracket body, the ligature being shown in open position prior to insertion of an arch wire in the arch wire slot.

For convenience and simplicity in description the embodiments are illustrated and described herein and claimed in the appended claims as they would be used in the lower central incisor region of a patient's mouth and in the conventional so-called labial technique, in which the brackets are attached to the labial surfaces of the teeth. The brackets of the invention are equally usable in the so-called lingual technique, in which they are attached to the teeth lingual surfaces so that they are concealed from view as much as possible; however when so used the slot opens to the lingual and not the labial, and the gingival and occlusal directions may also be reversed. Again for convenience in description the brackets are described as having specific named surfaces but, as is well known to those skilled in this art, it is usual in their manufacture wherever possible to avoid sharp edge junctions between the various surfaces, and they therefore usually merge smoothly with one another without a definite junction between them being apparent.

FIG. 1 shows in labial or lingual elevation a ligature of the invention for use with an orthodontic appliance such as an orthodontic bracket, the ligature comprising a coil spring hoop 10 of helically wound metal wire 10 having a corresponding hoop-shaped axis, the hoop being formed of metal wire wound helically around the hoop shaped axis, the ends of the wire from which the coil is wound being butted and welded together, as for example by laser welding, at their junction 12. The ligature is shown in unstressed state in which it has contracted until the coils are all in contact with one another. The size of the hoop in this unstressed state must be such that it will expand and fit snugly and elastically about the tie wings of a bracket; to this end the inside diameter 14 of the hoop is in the range from 1 mm to 5 mm (0.04 in to 0.20 in), while the outside diameter 16 of the helically wound coil of the hoop is in the range 0.40 mm to 1.0 mm (0.016 in to 0.040 in). The outside diameter 18 of the hoop will be the sum of these two diameters. The metal wire or strip from which the loop is formed usually has an effective diameter 20 in the range from 0.125 mm to 0.23 mm (0.005 in to 0.009 in). As shown in FIG. 1 the wire is of circular cross section and in that case its actual diameter is equal to its effective diameter; in other embodiments the cross section may be other than circular when the area of its cross section can be divided by Pi to give an equivalent effective diameter. There is no definite transition point at which a wire is more accurately described as a strip, and vice versa, in that a strip will usually be closer to rectangular than circular in transverse cross section, and therefore will usually have a greater difference than a wire between two dimensions at right angles, the larger dimension usually being referred to as the width while the smaller dimension is referred to as the thickness; for this reason both terms are used to describe the form of the metal that is used in the invention.

There are a number of ways known to those skilled in that particular art in which wire or strip ends can be connected together to form a complete hoop or torus, and a preferred form of connector is shown in FIG. 2, for use with metals that are difficult, or at present even impossible, to weld, braze or solder. It comprises an inner pin 22 which is threaded into the adjacent ends of a length of the coil from which the hoop is to be formed and an outer cylindrical sleeve 24 which is slipped over the adjacent coil ends and the pin 22. The sleeve 24 is then crimped radially inward toward the pin, as indicated by the arrows 26, with sufficient force to ensure that the coil ends are permanently retained within the connector. It will also be noted that the resulting unstrained hoop is not circular in elevation but can be described as more nearly square with rounded corners.

Another form taken by a ligature of the invention is shown in FIG. 3, in which it comprises a hoop shaped wave spring formed from metal strip or wire, the metal strip or wire being formed to a repeated successive wave shape along the length of the hoop. The ligature is shown in unstrained configuration in which the wave turns are at their minimum spacing, as they will be until the ligature is stretched around a bracket body. The metal from which the hoop is formed is usually of flatter cross section than that used for the ligature of FIG. 1 and, while the unstrained hoop or loop also has an inside diameter or dimension 28 in the range from 1 mm to 5 mm (0.04 in to 0.20 in), the wave amplitude 30 of the wave wound strip of the hoop is in the range 0.375 mm to 1.0 mm (0.015 in to 0.040 in), and the outside diameter 31 is the sum of dimensions 28 and 30. In this unstrained conformation the peak to peak spacing 32 is in the range 0.3 mm to 0.625 mm (0.012 in to 0.025 in) and the metal, which in this embodiment is more accurately a strip than a wire, has a thickness 34 in the range from 0.075 mm to 0.30 mm (0.003 in to 0.012 in) and a width 36 (see FIG. 27) in the range from 0.25 mm to 0.75 mm (0.010 in to 0.030 in). This embodiment will also have its ends joined by any suitable method including the two methods described above for the embodiments of FIGS. 1 and 2.

Stainless steels can be used for the ligatures of the invention, but care must be taken in their fabrication and use because of the relative ease with which quite small displacements produce large stresses in the strip or wire, to the extent that they can easily be overstressed when they may take a permanent "set" rendering them useless as operative springs. Preferably therefore the metal used is one of the so-called shape recovery metal alloys, also frequently called superelastic metal alloys, that have recently been developed and which are highly resistant to overstressing and permanent deformation, as compared to other metals. The "superelastic" stress-strain characteristic of such an alloy is shown in broken lines in FIG. 4, and the very flat shape will be noted. In particular, it will be noted from the Figure that above a relatively low stress value the application of additional stress causes a considerable increase in strain, so that if a strip or wire of this material is deflected by as much as 2 mm (which is a large deflection with such small springs), unlike a stainless steel, it returns to the non-deflected state with virtually no permanent set. Springs made of strips and wires of these alloys can be bent to a desired original "memory" shape and set in that shape by suitable heat treatment; subsequently if heated above a transformation temperature they will return to their original shape. The atomic structure which produces this phenomenon also causes these alloys to exhibit the so-called superelasticity, whereby when fabricated as a spring they are able to provide a relatively constant restoring force over the much wider ranges of deflection that they are able to tolerate.

A preferred family of shape memory alloys is superelastic nickel/titanium, usually with a nominal atomic composition of 50% nickel and 50% titanium, with small additions of copper, iron, cobalt or chromium, the alloy being subjected to a heat treatment to develop the desired characteristic. One particularly useful alloy in this family comprises 55% nickel and 45% titanium, while another comprises equal amounts of nickel and titanium with 10 atomic % of copper. Other alloys are also known such as titanium/molybdenum; copper/zinc/aluminium (usually 15–25 weight % zinc, 6–9 weight % aluminium and the balance copper); copper/zinc/aluminium/manganese; copper/aluminium/nickel (usually 13–14 weight % aluminium, 3–4 weight % nickel and the balance copper); and copper/aluminium/nickel/manganese. Other suitable alloys currently are sold under the Trade Names or Trade Marks REMATITAN; REMAINIUM; ELGILOY and TMA. At this time the nickel/titanium alloys are preferred in that they have the greatest ductility, more recoverable motion, excellent corrosion resistance comparable to series 300 stainless steels, stable transformation temperatures for shape recovery (memory) effect, high biocompatibility, and the ability to be electrically heated for shape recovery.

Stainless steels remain the metals of preference for the bracket body, if the body is to be of metal and not ceramic, since they are relatively inexpensive, as compared to the known shape memory metals, and the techniques for producing and working such metals are now well known. Thus the welding of a stainless steel ligature to a stainless steel bracket body presents no substantial technical difficulty since such welding is a relatively mature art. However, the welding of a ligature of a shape memory metal to a stainless steel body is very much more difficult and, until recently, it was considered that shape memory metals could not be welded, particularly since the heating would result in their immediate return to their recovery shape. However, Ge Wang of the Edison Welding Institute, Columbus, Ohio has recently reported from the Institute that it has proven possible to join "NITINOL", a nickel-titanium alloy to itself and also to stainless steel, and describes various methods for doing this with an outline of the precautions that must be observed.

FIG. 5 shows one way in which even better performance can be obtained from the coil spring ligatures of the invention by preloading the coil and heat treating it while in this preloaded state. Thus a coil wound normally as shown in FIG. 5A is wound even tighter to the configuration shown in FIG. 5B and then heat treated. This ensures that the stress provided by the spring does not drop to zero when the ligature is relatively unstrained, the unloading arm of the stress/strain characteristic now having the shape shown as a solid line in FIG. 4, the line crossing the stress axis at an elevated preload value. An equivalent effect can be obtained by arranging that the spring is of sufficient length that its turns will remain spaced from one another, even when used in combination with the smallest bracket and archwire, but the upper limit of the stress that can be provided is then reduced.

Figure 7:
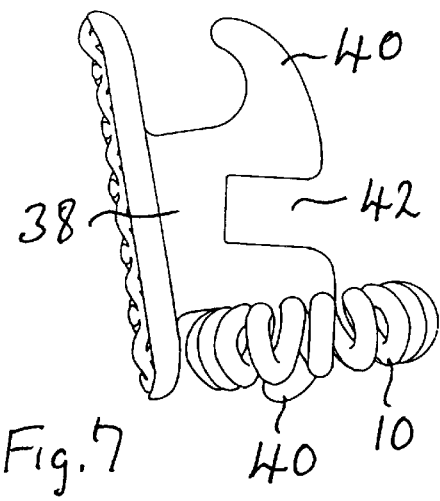
FIG. 7 is a mesial or distal elevation similar to FIG. 6 illustrating another way of mounting a coil spring ligature on the bracket body, the ligature also being shown in open position.
Figure 8:
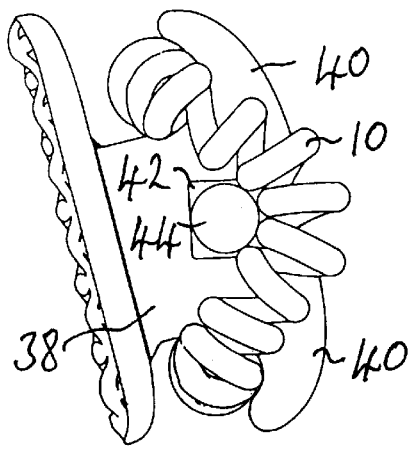
FIG. 8 is a mesial or distal elevation similar to FIGS. 6 and 7 showing the coil spring ligature in closed position and retaining an arch wire in the arch wire slot.

FIGS. 6 through 8 show the use of a coil spring ligature 10 with a standard "Siamese twin" bracket 38 comprising two mesially-distally spaced pairs of occlusal-gingival extending tie wings 40 and a mesially-distally extending arch wire slot 42 that opens to the labial. The ligature can be looped over the occlusal extending tie wings (FIG. 6) or the gingival extending tie wings (FIG. 7) and will remain in a slot open position in which the labial slot opening is open to permit the insertion therein, or the removal therethrough, of an arch wire 44 of the required cross section. Once the arch wire is in place the ligature can be engaged over the other tie wings, as shown in FIG. 8, to retain the arch wire in the slot and, if in any way misplaced in the slot, to urge it into contact with the slot lingual wall.

Figure 9:
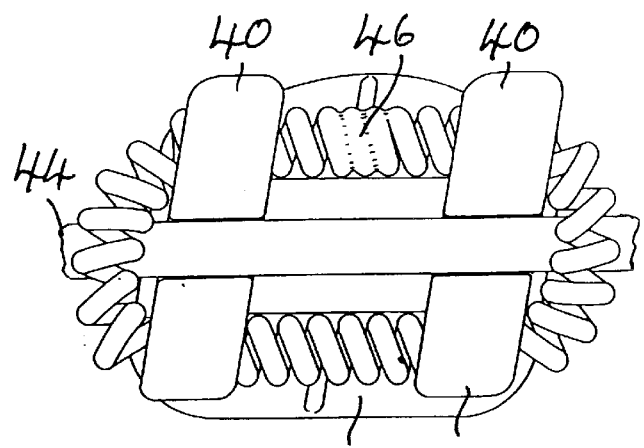
FIG. 9 is an elevation from the labial showing an embodiment in which a coil spring ligature hoop is permanently attached to a bracket body of the bracket and ligature of FIG. 8.

In view of the extended life to be expected from the metal ligatures of the invention it is possible to fasten them to the bracket body to result in a self-ligating bracket, and such a combination is shown in FIG. 9. The ligature has the form of a hoop or torus and is fastened to the bracket body at a location 46, as by welding for a metal bracket or a suitable cement for a non-metal bracket, the preferred location being between either of the two pairs of tie wings 40, so that with the ligature in open position the bracket and ligature combination appears as in FIG. 6 or 7.

Figure 10:
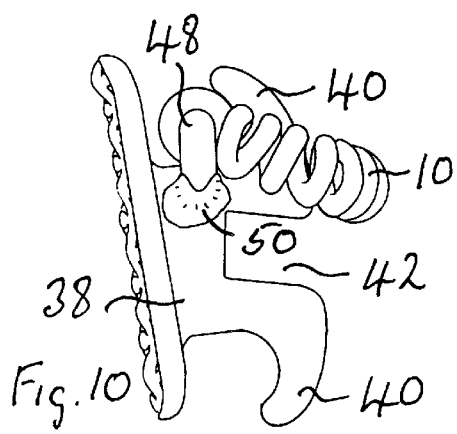
FIGS. 10 and 11 are mesial or distal elevations showing the mounting of a coil spring hoop on a bracket body, the hoop being shown respectively in open and closed positions.
Figure 11:
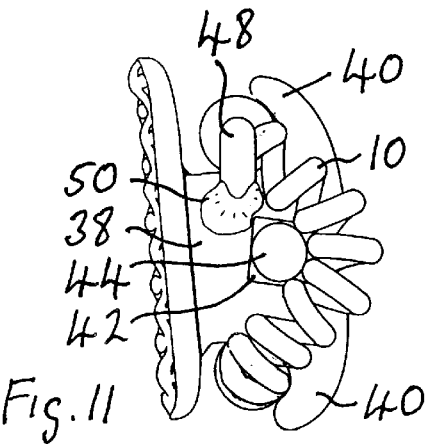
Figure 12:
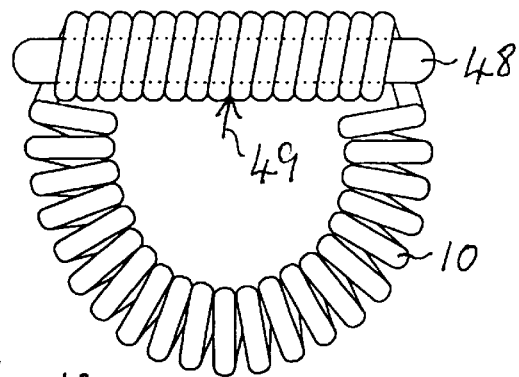
FIG. 12 is a front elevation of a coil spring hoop of the embodiment of FIGS. 10 and 11 ready for attachment to a bracket body.
Figure 13:
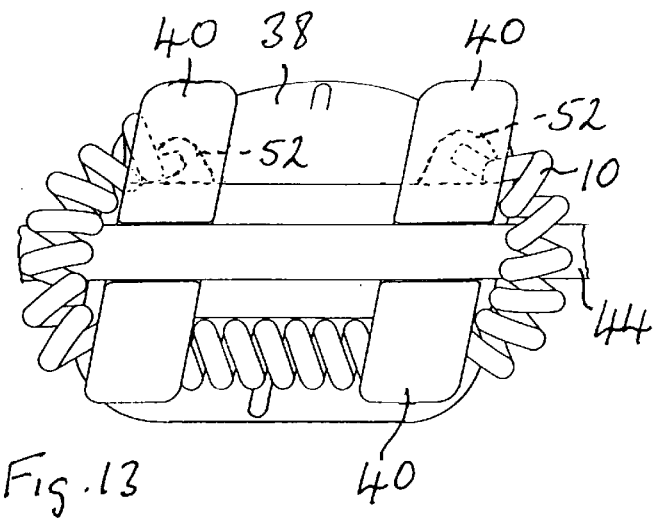
FIG. 13 is an elevation from the labial similar to FIG. 9 and showing another way in which a coil spring ligature loop is permanently attached to a bracket body.

FIGS. 10 through 12 show a self-ligating bracket in which a length of coil spring is attached to the bracket body via a U-shaped core member 48 on the opposite ends of which the length are threaded until they butt together at the centre 49 of the core member, the core member ends then being fastened at 50 to the bracket body, again as by welding or a suitable cement. In another embodiment shown in FIG. 13 the ligature comprises a loop 10 of the wire coil having its free ends fastened at 52, again as by welding or a suitable cement, to the mesial and distal sides of the bracket.

Figure 14:
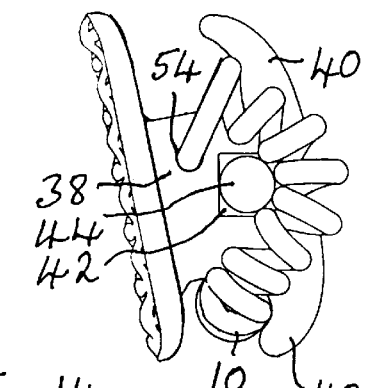
FIG. 14 is a mesial or distal elevation of a bracket showing a further way in which a coil spring ligature is attached to the body.

FIG. 14 shows a method of permanently attaching a ligature to a bracket that is particularly suited for brackets made of ceramic, plastics, composite and similar materials, with which welding is not possible and when cements may not be able to provide the necessary strength of attachment. The bracket body is provided with a mesial distal extending bore 54 disposed between and spaced from the bracket occlusal, lingual and labial surfaces and the arch wire slot occlusal and lingual surfaces. The bore is completely surrounded by the body and can be made relatively very large in transverse dimension without compromising the strength of the body. The ends of the coil loop are unwound and inserted into the bore, where a relatively low strength cement will be able to provide secure attachment.

Figure 15:
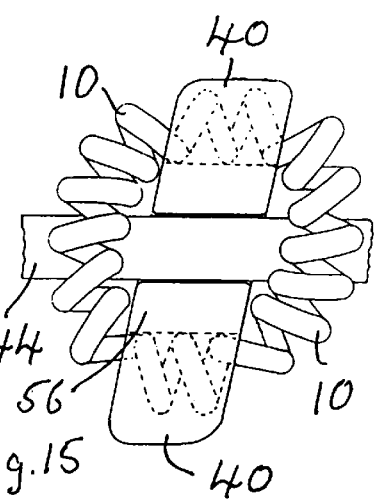
FIG. 15 is an elevation from the labial showing the application of a coil spring ligature hoop to a single tie wing bracket body.

FIG. 15 shows the application of a coil spring ligature of the invention to a so-called "single" bracket 56 having a single pair of tie wings 40. The ligature can be used separately from the bracket or can be permanently attached, as described above, to provide a self-ligating bracket.

In the bracket/ligature combinations shown above the ligature in the slot closed position directly engages the arch wire 44 in the slot so that inevitably there is sliding friction between them inhibiting movement of the bracket mesially or distally along the wire, and therefore inhibiting corresponding movement of the teeth to which the brackets are attached. Many procedures require that at least at some stage any such friction is minimized, or is controlled, or even removed completely, so that the teeth can move mesially or distally with a corresponding degree of freedom during this stage. This can be accomplished by use of the ligature/attachment combinations shown in FIGS. 16 through 24, wherein the ligature urges an attachment 58 into contact with the labial surfaces of the tie wings, the gingival-occlusal height of the attachment being greater than the corresponding height of the arch wire slot. Thus, as long as the arch wire protrudes from the arch wire slot the ligature and the attachment will be effective to urge the arch wire into the required orientation within the slot and, as soon as that has been accomplished, the bracket will be free to slide with the required degree of freedom along the arch wire.

Figure 16:
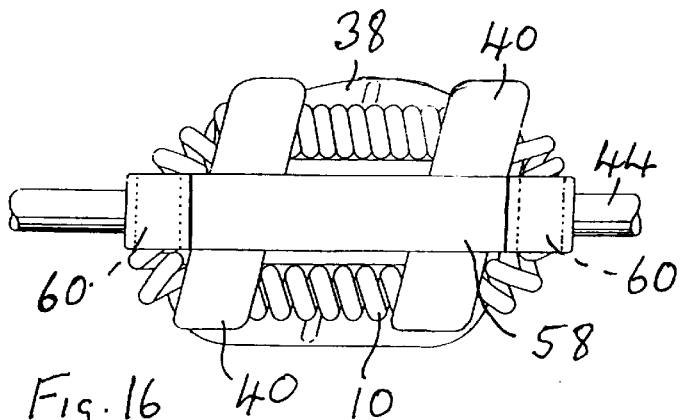
FIG. 16 is an elevation from the labial showing a coil spring ligature hoop mounted on a bracket and comprising an attachment thereto to provide friction-free operation of the orthodontic procedure, the ligature being in slot closed position.
Figure 17:
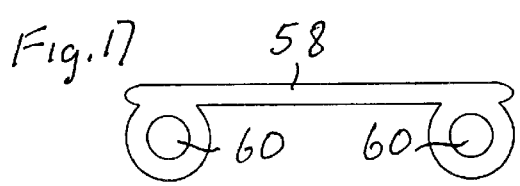
FIG. 17 is a view from the occlusal or gingival of the attachment employed in the embodiment of FIG. 16.
Figure 18:
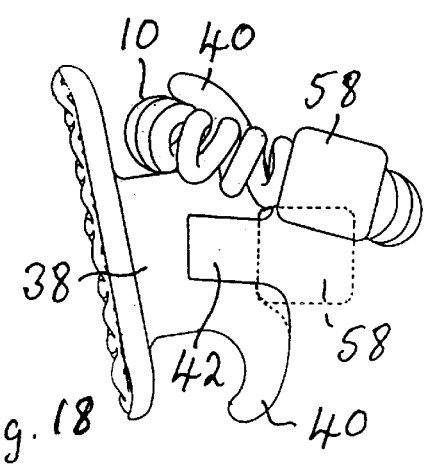
FIG. 18 is a mesial or distal elevation of the bracket of FIG. 16 showing the coil spring ligature and its attachment in slot open position and the attachment alone in broken lines in slot closed position.

In the embodiment of FIGS. 16–18 the attachment 58 has a rectangular body that is elongated in the mesial-distal direction and has two cylindrical bores 60 respectively at its ends of suitable diameter for the ligature coil to pass through. FIG. 16 shows the ligature in closed position with the attachment butting against the bracket body labial surface, while FIG. 18 shows it in solid lines in open position. FIGS. 19–21 show the form taken by the attachment 58 when it is required to provide a controlled amount of friction. The attachment body is provided on the surface that faces the arch wire slot lingual surface with an elongated protrusion 62 that, when the ligature/attachment combination is in the slot closed position, shown for the attachment only in broken lines in FIG. 19, the protrusion will engage the arch wire with a degree of friction determined by the labial-lingual dimension of the slot, the corresponding dimension of the arch wire, and the corresponding dimension of the protrusion. In the embodiment of FIGS. 22–24 the attachment body 58 is provided with holes 64 through which the wire forming the coil 10 is threaded to retain the attachment on the hoop, while a protrusion 66, if provided, has the form of a hump or mound of about the same mesial-distal dimension as its occlusal-gingival dimension, the hump location being closer to one pair of tie wings than to the other. In these embodiments also the ligature 10 can be permanently attached to the bracket body, and an additional manner of attachment is by a wire (not shown) threaded through the wire coil and wound around the bracket post 67.

FIG. 25 shows the application of the wave wound spring of FIG. 3 to a standard Siamese twin bracket 38, to which it can be permanently attached if required, as described above. FIGS. 26 and 27 show a preferred form of wave spring ligature, again for use separately or attached to the bracket body, it being shown attached in FIG. 26 at location 68. As is most clearly seen from FIG. 27 the ligature comprises an attachment part 70 which is attached, again as by welding or cementing at 68 to the bracket body 38, but which otherwise would engage behind and be retained by the adjacent pair of tie wings 40. The attachment part is connected at its ends by two mesially distally spaced wave spring portions 10 to an integral loop retainer part 72 which, in the slot closed position shown in FIG. 26, is looped over the other pair of tie wings 40 to retain the ligature in that position.

I claim:

1. A ligature for an orthodontic appliance comprising a hoop shaped coil spring of metal strip or wire having a corresponding hoped shaped axis, the metal strip or wire being wound helically about the hoop shaped axis;

wherein the unstrained hoop shaped coil has an inside diameter in the range from 1 mm to 5 mm (0.04 in to 0.20 in) and the helically wound coil has an outside diameter in the range 0.40 mm to 1.0 mm (0.016 in to 0.040 in).

2. A ligature as claimed in claim 1, wherein the metal from which the ligature is made is a shape memory metal.

3. A ligature as claimed in claim 1, wherein the metal strip or wire has a diameter, or an equivalent effective diameter as defined herein, in the range from 0.125 mm to 0.23 mm (0.005 in to 0.009 in).

4. A ligature for an orthodontic appliance comprising a hoop shaped wave spring of metal strip or wire, the metal strip or wire being formed to a repeated successive wave along the length of the hoop;

wherein the unstressed hoop has an inside diameter in the range from 1 mm to 5 mm (0.04 in to 0.20 in) and the amplitude of the waves of the wave wound strip or wire of the hoop is in the range 0.375 mm to 1.0 mm (0.015 in to 0.040 in).

5. A ligature as claimed in claim 4, wherein the metal from which the ligature is made is a shape memory metal.

6. A ligature as claimed in claim 4, wherein the metal strip or wire has a thickness in the range from 0.075 mm to 0.30 mm (0.003 in to 0.012 in) and a width in the range from 0.25 mm to 0.75 mm (0.010 in to 0.030 in).

7. An orthodontic bracket comprising:

a bracket body having labial, lingual, gingival, occlusal, mesial and distal surface portions, the body having a mesial distal extending arch wire slot opening to the labial surface portion; and a ligature attached to the body and movable on the body between open and closed positions in which the slot opening respectively is open for insertion of an arch wire into the slot and its removal therefrom, and is closed by the ligature to retain an arch wire therein;

the ligature comprising a hoop or loop shaped coil spring of metal strip or wire having a corresponding hoop or loop shaped axis, the metal strip or wire being wound helically about the hoop or loop shaped axis.

8. A bracket as claimed in claim 7, wherein the metal from which the ligature is made is a shape memory metal.

9. A bracket as claimed in claim 7, wherein the unstrained hoop or loop has an inside diameter in the range from 1 mm to 5 mm (0.04 in to 0.20 in) and the helically wound coil of the hoop or loop has an outside diameter in the range 0.40 mm to 1.0 mm (0.016 in to 0.040 in).

10. A bracket as claimed in claim 9, wherein the metal strip or wire has a diameter, or an equivalent effective diameter as defined herein, in the range from 0.125 mm to 0.23 mm (0.005 in to 0.009 in).

11. A bracket as claimed in claim 7, wherein the metal strip or wire has a diameter, of an equivalent effective diameter as defined herein, in the range from 0.125 mm to 0.23 mm (0.005 in to 0.009 in).

12. A bracket as claimed in claim 7, wherein the ligature has the form of a hoop and is attached to the bracket body via a U-shaped core member threaded through part of the hoop and having its ends fastened to the bracket body.

13. A bracket as claimed in claim 7, wherein the ligature has the form of a loop having its ends inserted in respective bores in the bracket body.

14. An orthodontic bracket comprising:

a bracket body having labial, lingual, gingival, occlusal, mesial and distal surface portions, the body having a mesial distal extending arch wire slot opening to the labial surface portion; and a ligature attached to the body and movable on the body between open and closed positions in which the slot opening is respectively open for insertion of an arch wire into the slot and its removal therefrom and is closed by the ligature to retain an archwire therein;

the ligature comprising a hoop or loop shaped wave spring of metal strip or wire, the metal strip or wire being formed to a repeated successive wave shape along the length of the hoop or loop.

15. A bracket as claimed in claim 14, wherein the metal from which the ligature is made is a shape memory metal.

16. A bracket as claimed in claim 14, wherein the unstrained hoop or loop has an inside diameter in the range from 1 mm to 5 mm (0.04 in to 0.20 in) and the amplitude of the waves of the wave wound strip is in the range 0.375 mm to 1.0 mm (0.015 in to 0.040 in).

17. A bracket as claimed in claim 16, wherein the metal strip or wire has a thickness in the range from 0.075 mm to 0.30 mm (0.003 in to 0.012 in) and a width in the range from 0.25 mm to 0.75 mm (0.010 in to 0.030 in).

18. A bracket as claimed in claim 14, wherein the metal strip or wire has a thickness in the range from 0.075 mm to 0.30 mm (0.003 in to 0.012 in) and a width in the range from 0.25 mm to 0.75 mm (0.010 in to 0.030 in).

19. A bracket as claimed in claim 14, and comprising at least one pair of occlusal-gingival extending tie wings protruding from the bracket body on opposite sides of the arch wire slot and for reception of a ligature, wherein the ligature comprises an attachment part by which it is attached to the bracket body and a loop retainer part engageable over one of the tie wings so as to retain the ligature in the closed position, the attachment and retainer parts being connected together by two mesially-distally spaced wave wound spring parts that with the ligature in closed position extend over the arch wire slot opening.

\* \* \* \* \*

UNITED STATES PATENT AND TRADEMARK OFFICE
CERTIFICATE OF CORRECTION

PATENT NO. : 5,885,074
DATED : 23 March, 1999
INVENTOR(S) : Eric H. HANSON

It is certified that error appears in the above-identified patent and that said Letters Patent is hereby corrected as shown below:

Column 8, Line 44, Claim 1  Amend "hoped" to --hoop--

Signed and Sealed this

Twenty-seventh Day of July, 1999

Attest:

Q. TODD DICKINSON

*Attesting Officer*    *Acting Commissioner of Patents and Trademarks*